Figure 1:
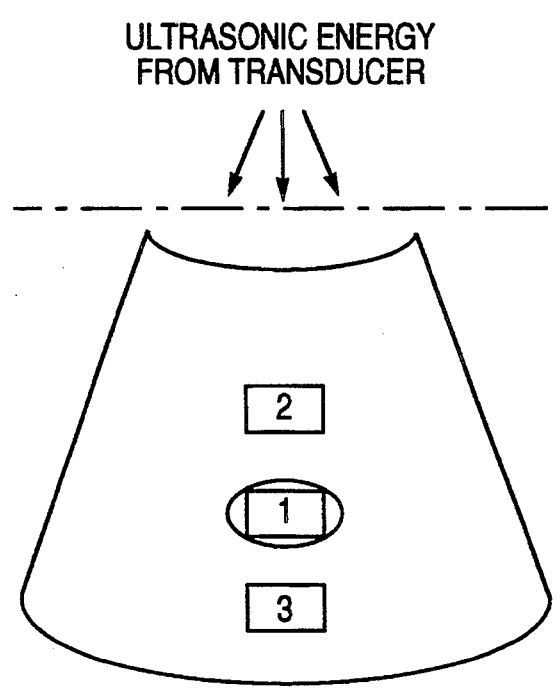

United States Patent [19]

Anderson et al.

[11] Patent Number: 5,385,147
[45] Date of Patent: Jan. 31, 1995

[54] METHOD OF ULTRASONIC IMAGING OF THE GASTROINTESTINAL TRACT AND UPPER ABDOMINAL ORGANS USING AN ORALLY ADMINISTERED NEGATIVE CONTRAST MEDIUM

[75] Inventors: Leslie D. Anderson, Encinitas; Janeth M. Bartlett; Diane M. Szaflarski, both of San Diego; Kenneth J. Widder, Rancho Santa Fe, all of Calif.

[73] Assignee: Molecular Biosystems, Inc., San Diego, Calif.

[21] Appl. No.: 125,621

[22] Filed: Sep. 22, 1993

[51] Int. Cl.$^6$ .............................................. A61B 8/00
[52] U.S. Cl. .............................................. 128/662.02
[58] Field of Search ............... 128/660.01, 660.06, 128/662.02, 661.02; 424/439, 9

[56] References Cited

U.S. PATENT DOCUMENTS

| | | | |
|---|---|---|---|
| 4,774,958 | 10/1988 | Feinstein | 128/660.01 |
| 4,844,882 | 7/1989 | Widder et al. | 128/660.01 |
| 4,957,656 | 9/1990 | Cerny et al. | 128/662.02 |
| 5,059,416 | 10/1991 | Cherukuri et al. | 424/439 |
| 5,107,842 | 4/1992 | Levene et al. | 128/662.02 |
| 5,179,955 | 1/1993 | Levene et al. | 128/662.02 |
| 5,179,995 | 1/1993 | Limb | 164/114 |
| 5,230,882 | 7/1993 | Unger | 128/662.02 |

FOREIGN PATENT DOCUMENTS

| | | | |
|---|---|---|---|
| 3246386 | 6/1984 | Germany | 128/660.01 |
| WO91/18612 | 12/1991 | WIPO | 128/660.01 |

OTHER PUBLICATIONS

Von Helzel, "Early experience with the use of 'contrast media' for use in ultrasound examination of the upper abdomen" *Fortschr. Rontgenstr.* (1984) 140:337–340.

Stringer et al., "Sonography of the normal and abnormal stomach (excluding hypertrophic pyloric stenosis) in children" *J. Ultrasound Med.* (1986) 5:183–188.

Warren et al., "The liquid–filled stomach—an ultrasonic window to the upper abdomen" *J. Clin. Ultrasound* (1978) 6:315–320.

Worlicek et al., "Ultrasonic examination of the wall of the fluid filled stomach" *J. Clin. Ultrasound* (1989) 17:5–14.

Miyamoto et al., "Ultrasonographic findings in gastric cancer: in vitro and in vivo studies" *J. Clin. Ultrasound* (1989) 17:309–318.

Lembcke et al., "Role of gastrointestinal transit in the delay of absorption by viscous fibre (guar)" *Hepato-gastroenterology* (1984) 31:183–186.

Bolondi et al., "Measurement of gastric emptying time by real-time ultrasonography" *Gastroenterology* (1989) 89:752–759.

Hunt, "Does calcium mediate slowing of gastric emptying by fat in humans?" *Am. J. Physiol.* (1983) 244:G89–G94.

Brener et al., "Regulation of the gastric emptying of glucose" *Gastroenterology* (1983) 85(1):76–82.

Brogna et al., "Comparison between gastric emptying of digestible and indigestible solids in diabetic patients" *Acta diabetol. lat.* (1990) 27:255–259.

Chang et al., "Physical properties of starch meals in vivo and in vitro and their influence on gastric emptying and oral glucose tolerance test" *Nutrition* (1990) 7(6):410–416.

Chaudhari et al., "Update: pharmaceuticals and gastric emptying" *Am. J. Gastroenterology* (1990) 85(3):223–230.

(List continued on next page.)

*Primary Examiner*—George Manuel
*Attorney, Agent, or Firm*—Morrison & Foerster

[57] ABSTRACT

A method for enhanced ultrasonic imaging of the tissues defining the gastrointestinal tract and the upper abdominal organs wherein the gastrointestinal tract is filled with a chemically defined essentially sonolucent ultrasound contrast agent that is stable under gastric conditions and has a gastric emptying time of at least about twenty minutes, thus causing the lumen of the upper gastrointestinal tract to appear dark relative to the positive image of the gastrointestinal tract walls and upper abdominal organs.

19 Claims, 2 Drawing Sheets

Cunningham et al., "The effect of short-term dietary supplementation with glucose on gastric emptying in humans" *Brit. J. Nutrition* (1991) 65:15–19.

Davenport, "Gastric digestion and emptying; absorption" *Physiology of the Digestive Tract* (1977) Chapter 13, pp. 187–197.

Dickerson et al., "Osmolality of oral drug solutions and suspspensions" *Am. J. Hosp. Pharm.* (1988) 45:832–834.

Edwards et al., "Viscosity of food gums determined in vitro related to their hypoglycemic actions" *Am. J. Clin. Nutr.* (1987) 46:72–77.

Fisher et al., "Effect of hydrochlorides of amino acids in test meals on gastric emptying" *Digestion* (1977) 16:18–22.

Fisher et al., "Gastric emptying of a physiologic mixed solid–liquid meal" *Clin. Nucl. Med.* (1982) 7(5):215–221.

Gould et al., "A model of gastric emptying in cats shows solid emptying is promoted by MK-329: a CCK antagonist" *J. Nucl. Med.* (1990) 31(9):1494–1500.

Harju, "Increases in meal viscosity caused by addition of guar gum decrease postprandiale acidity and rate of emptying of gastric contents in healthy subjects" *Panminerva Medica* (1985) 27:125–128.

Itani et al., "Osmocaloric regulation of gastric emptying after duodenojejunostomy: interplay with the gastric funds" *Surgical Forum* pp. 131–135.

Jonderko, "Comparative analysis of quantitative gastric emptying indices and power-exponential modelling of gastric emptying curves" *Clin. Phys. Physiol. Meas.* (1989) 10(2):161–170.

Kasper et al., "The influence of dietary fiber on gastric transit time" *Hepatogastroenterology* (1985) 32:69–71.

Keller et al., "Successful left ventricular opacification following peripheral venous injection of sonicated contract agent: an experimental evaluation" *Am. Heart J.* (1987) 114(3):570–575.

Lawaetz et al., "Effect of pectin on gastric emptying and gut hormone release in the dumping syndrome" *Scamd. J. Gastroenterol.* (1993) 18:327–336.

Malagelada, "Where do we stand on gastric motility?" *Scand. J. Gastroenterol.* (1990) 25(Suppl. 175):42–51.

McHugh et al., "Calories and gastric emptying: a regulatory capacity with implications for feeding" *Am. Physiol. Soc.* (1979) pp. R254–R260.

McHugh et al., "Postpyloric regulation of gastric emptying in rhesus monkeys" *The Am. Physiol. Soc.* (1982) pp. R408–R415.

Meyer et al., "Intragasic vs. intraintestinal viscous polymers and glucose tolerance after liquid meals of glucose" *Am. Soc. Clin. Nutrition* (1988) 48: 260–266.

Minami et al., "The physiology and pathophysiology of gastric emptying in humans" *Gastroenterology* (1984) 86:1592–1610.

Noakes et al., "The importance of volume in regulating gastric emptying" *Med. Sci. Sports Exer.* (1991) 23(3):307–313.

Ophir et al., "Contrast agents in diagnostic ultrasound" *Ultrasound in Med. & Biol.* (1989) 15(4):319–333.

Phillips et al., "Linear gastric emptying of hyperosmolar glucose solutions" *J. Nucl. Med.* (1991) 32(3):377–381.

Reilly et al., "Gastric emptying of liquids and solids in the portal hypertensive rat" *Digest. Dis. Sci.* (1990) 35(6):781–786.

Russell et al., "Canine gastric emptying of fiber meals: influence of meal viscosity and antroduodenal motility" *Am. Physiol. Soc.* (1985) pp. G662–G667.

Sandhu et al., "Effect on gastric emptying and gastroduodenal motility in normal subjects" *Gastroenterology* (1987) 92:486–492.

Schade et al., "Technetium-99m carboxymethylcellulose: a newly developed fibre marker for gastric emptying studies" *Eur. J. Nucl. Med.* (1991) 18:380–384.

Shafer et al., "Do calories, osmolality, or calcium determine gastric emptying?" *Am. J. Physiol.* (1985) pp. R479–R483.

Sole et al., "Faster gastric emptying for glucose-polymer and fructose solutions than for glucose in humans" *Eur. J. Appl. Physiol.* (1989) 58:605–612.

Tatsuta et al., "Gastric emptying in patients with fundal gastritis and gastric cancer" *Gut* (1990) 31:767–769.

Taylor, "Gastric emptying, fibre, and absorption" *The Lancet* (1979) p. 872.

Weighall et al., "The fluid–filled stomach: a new sonic window" *J. Clin. Ultrasound* (1979) 7:353–356.

Wulschke et al., "The control mechanisms of gastric emptying are not overridden by motor stimulants" *Am. Physiol. Soc.* (1986) pp. G744–G751.

METHOD OF ULTRASONIC IMAGING OF THE GASTROINTESTINAL TRACT AND UPPER ABDOMINAL ORGANS USING AN ORALLY ADMINISTERED NEGATIVE CONTRAST MEDIUM

DESCRIPTION

TECHNICAL FIELD

This invention is in the field of ultrasonic imaging of the human body for diagnostic purposes. More particularly it relates to methods for ultrasonically imaging the tissue defining the stomach and tissues and organs proximal thereto by using a negative contrast medium to fill the gastrointestinal tract in order to render the lumen therein transparent to ultrasound waves.

BACKGROUND

Ultrasonic imaging uses an ultrasonic scanner to generate and receive sound waves. A transducer is placed on a body surface overlying the region to be imaged, and ultrasonic energy is directed toward that area. As ultrasonic energy penetrates the body, the velocity of the energy and acoustic properties of the body tissue and organs encountered by the energy determine the degree of absorption, scattering, transmission and reflection of the energy. The characteristics of ultrasonic energy reflected back to the transducer are then transformed into the ultrasonic image.

As ultrasound waves move through one substance to another, there is some degree of reflection at the interfaces. The degree of reflection is related to the acoustic properties of the substances defining the interface. If these properties differ, such as with a liquid-solid or liquid-gas interface, the degree of reflection is enhanced. Body tissues and organs that do not reflect ultrasound energy due to their ability to transmit or absorb the energy appear dark in the image whereas body tissues and organs that reflect the energy appear light in the image. These images may be enhanced by the use of contrast agents.

Imaging of the gastrointestinal tract and surrounding tissues/organs can be difficult due to the presence of acoustically reflective gas bubbles. This problem can be overcome by having the subject ingest a contrast agent which fills the stomach and displaces the gas.

There are two general types of ultrasound contrast agents; positive contrast agents and negative contrast agents. Positive contrast agents reflect the ultrasonic energy and thus they produce a positive (light) image. Correspondingly, negative contrast agents enhance transmissibility or sonolucency and thus produce a negative (dark) image. The sonolucency of an orally administered negative contrast agent contained within the gastrointestinal tract will improve the visualization of the surrounding tissues and organs as well as the tissues defining the gastrointestinal wall.

Several publications disclose orally administered positive contrast agents. A German patent application and article by Helzel (German Pat. Appln. 3246386 A1 and Fortschr. Rontgenstr. (1984) 140:337–340) describe the use of various aqueous emulsions and particulate suspensions as orally administered positive contrast agents. More recently, U.S. Pat. Nos. 5,107,842 and 5,179,995 describe the use of aqueous suspensions, particulate vegetable substances, clays, and hydrocolloids as positive contrast agents. PCT application no. PCT/US91/03850 (Pub. No. WO 91/18612) describes aqueous mixtures of biocompatible polymers, preferably coated with silicon-containing compounds, as orally administered positive contrast agents.

Similarly, there are several prior publications which describe attempts to improve the transmission of ultrasound through the stomach lumen to improve imaging of the stomach wall and upper abdominal organs by filling the stomach with fluids. Stringer et al., J. Ultrasound Med. (1986) 5:183–188 describe ultrasound imaging of children's stomachs into which water with glucose had been introduced. Warren et al., J. Clin. Ultrasound (1978) 6:315–320 report attempts to make the stomach lumen an "ultrasonic window" by filling it with a 1% aqueous mixture of methylcellulose and administering butylscopolamine bromide (Bucospan) i.v. to inhibit peristalsis. The article indicates the methylcellulose forms mucilages in the mixture. While it is reported the mixture "allows good through-transmission of sound", the ultrasound images presented in the article show that the mucilages reflect energy and appear as white granular bodies. Worlicek et al., J. Clin. Ultrasound (1989) 17:5–14 describe ultrasonic imaging of patients who have ingested orange juice and been injected i.v. with butylscopolamine bromide. Miyamoto et al., J. Clin. Ultrasound (1989) 17:309–318 describe ultrasonic imaging of the stomachs of patients who had ingested deaerated water and received a butylscopolamine bromide injection.

These fluids all exhibit rapid gastric emptying thus requiring concomitant injection of an antispasmodic agent to inhibit peristalsis. They also include materials that are echogenic and thus give a positive image (e.g., methylcellulose mucilages, orange juice pulp). In addition they are not chemically defined (orange juice) and thus cannot be expected to provide reproducible enhancement of images.

DISCLOSURE OF THE INVENTION

The present invention involves the use of a chemically defined essentially sonolucent and nonechogenic aqueous contrast agent solution in ultrasonic imaging of the gastrointestinal tract and upper abdominal organs. These solutions are stable under gastric conditions, and have an inherent gastric retention time of at least about twenty minutes. More specifically, the invention is a method of ultrasonic imaging of tissue defining the upper gastrointestinal tract, particularly the stomach, and the surrounding upper abdominal organs. It requires introducing the aqueous essentially sonolucent contrast agent solution into the stomach, applying ultrasonic energy to the stomach and upper abdomen while the solution is present in the upper gastrointestinal tract, and forming an image from the energy which passes through the solution and is reflected by the tissues and organs.

MODES FOR CARRYING OUT THE INVENTION

The solutions that are used in the invention method possess a combination of acoustic, chemical and physiological properties that render them suitable for use as negative ultrasound contrast media. When introduced into the gastrointestinal tract, they provide an acoustic window of transmission to the tissue defining the gastrointestinal tract and tissues/organs adjacent thereto. The acoustic properties necessary for solutions to be useful in the present invention are sonolucency and nonechogenicity. This means that the solution must freely transmit the ultrasound energy with low levels of attenuation (sonolucent) and produce little backscatter (nonechogenic). These combined properties will result in the production of a negative image.

Backscatter is a measure of the echogenicity of the solution and may be expressed as a backscatter factor. Backscatter is normally associated with the presence of entrained gas bubbles and/or particulate matter (either liquid, gel, or solid) in the solution. The solutions used in the present invention exhibit low degrees of backscatter, because they are essentially free of gas bubbles and particulate matter.

Attenuation is a measure of the absorption of the ultrasonic energy by a solution and may be affected by the concentration of solute in the solution, the viscosity of the solution and/or the temperature of the solution. If the ultrasound energy is significantly attenuated during its transmission through the solution, it will diminish the backscattering signal causing it to be artificially low. Significant attenuation would not allow for imaging of tissues/organs beyond the body cavity containing the solution. If a solution causes significant attenuation, it would not be considered sonolucent.

The degree of attenuation and backscatter of solutions can be measured in vitro by any known method. One such method involving the use of a phantom as described in Example 2. However, any other suitable method can be used to determine that the solutions are essentially sonolucent and nonechogenic, using degassed water as a standard solution which meets both of these criteria. A solution which exhibits no more than about 20% backscatter in vitro relative to degassed water and a solution which exhibits no more than about 25% attenuation in vitro is considered nonechogenic.

Gastric emptying time of a solution is a function of the rate at which the contents of the stomach empty and is the time it takes for the contents of the stomach to empty into the small bowel. Ways of measuring gastric emptying time are known in the art (see, for example, B. Lambcke et al., Hepato-gastroenterology 31 (1984) 183–186; L. Bolondi et al. Gastroenterology 89 (1985) 752–759). One way is provided in Example 3, wherein gastric emptying time is expressed as the amount of time the stomach remains distended after ingestion of the solution. The solutions of the present invention exhibit a gastric emptying time of greater than 20 minutes, preferably 30 minutes to 45 minutes, in the absence of coadministration of antiperistaltic agents such as butylscopolamine bromide. A gastric emptying time of twenty minutes or more is necessary to enable the sonographer to perform the ultrasound examination while the solution is present in the stomach. During the examination process, which may take one half to one hour, the sonographer can also image the small bowel as the solution empties from the stomach.

The rate of gastric emptying is influenced by the volume and contents of the stomach. Minarin et al. (Gastroenterology 86:1592–1610, 1984) describe factors that increase gastric emptying time as being high osmolality, pH, the presence of certain amino acids (such as L-tryptophan), the presence of fats (such as fatty acids), and caloric content. Interaction of these substances with specific receptors in the small bowel is believed to be the basis for this effect.

The relatively long gastric emptying time of the medium described herein may be achieved by increasing osmolality, acidity, caloric content and/or the inclusion of other solutes such as amino acids, fatty acids, glycerides (including mono-, di- and triglycerides) and agents that bind calcium ions. Fatty acids and agents that bind calcium ions at gastric pHs are known in the art (see, for example, J. N. Hunt, Am. J. Physiol. 244 (Gastrointest. Liver Physiol. 7):G89–G94, 1983). Preferably the solution is hyperosmolar, i.e., has an osmolality above about 300 millimoles per kilogram (mmol/kg).

The osmolality of a solution is defined as the total number of solute particles dissolved in one kilogram of solvent, and is independent of the physical properties of the particles such as size, density, configuration, or electrical charge.

Examples of solutes which may be used either alone or in combination to make hyperosmolar solutions are polydextrose, maltodextrin, corn syrup, and glycerin. Although the concentration of the particular solute(s) used will depend on its (their) molecular weight, typical concentrations will normally be in the range of 10% to 50% w/v. The solutions may also contain preservatives, colorants, sweeteners or other additives which enhance their stability or palatability without adversely affecting their acoustical properties.

The solutions may be made by mixing the solute and other additives with water, optionally with heating to facilitate complete solubilization of the solute and additives. The solution may then be degassed, such as by subjecting the solution to vacuum. It should be noted that the solutions of the invention are chemically defined, meaning that their chemical compositions are predetermined, known, and reproducible. In this regard aqueous mixtures of variable and undefined chemical composition, such as fruit juices, are not commercially useful as contrast agents as they may contain particulate matter. Accordingly, such chemically undefined fluids are not within the present invention.

In use, the solution is introduced into the stomach of a fasting patient by ingestion or intubation, preferably the former. The volume of solution introduced should be sufficient to substantially fill the stomach (typically 100 to 1000 mL, preferably 250–500 mL for adults and 100–300 mL for children) and displace the gas therein. Gas is removed from the imaging fluid by any of a combination of chemical displacement, dispersion, and absorption into the solution. The upper abdomen is then scanned with conventional ultrasound diagnostic equipment to produce an image of the upper gastrointestinal tract and if desired any of the upper abdominal organs (e.g., pancreas, spleen, portions of kidney). As indicated, due to the presence of the sonolucent solution in the upper gastrointestinal tract, the sonographer is able to obtain enhanced images of the gastrointestinal tract walls and adjacent abdominal tissues/organs. Because of its sonolucency and nonechogenicity in a normal B mode scan, the solution appears dark and decreases artifactual positive signal. The ultrasonic images obtained using the solution of the present invention may be used to detect or monitor disease or other abnormalities in the tissues or organs being visualized.

The solutions have chemical properties that render them shelf-stable at ambient temperatures for periods of up to a year or more, are stable under gastric conditions (i.e., do not form precipitates at the pH and temperature of the stomach, do not react with gastric fluids to form gas, and do not react within the stomach to adversely affect the sonolucency of the medium), displace gas from the stomach, and are nontoxic and nonirritating.

The invention is further illustrated by the following examples. These examples are not intended to limit the invention in any manner.

EXAMPLE 1

Sample Preparation and Osmolality Determination

One liter batches of each sample were prepared according to the concentrations outlined in Table 1 below by adding the ingredients to water and mixing to homogeneity. The solutions also contained 0.2% w/v preservatives which may have contributed to the osmolality of the solutions.

The osmolality of each solution was determined using a Wescor (Logan, Utah) Vapor Pressure Osmometer 5500 according to manufacturer's directions. The results are reported below in Table 1.

TABLE 1

| Osmolality Results | |
|---|---|
| Solution | Osmolality (mmol/kg) |
| Polydextrose, 25% w/v | 589 |
| Maltodextrin, 48.5% w/v | 740 |
| Corn Syrup, 15.75% v/v | 521 |
| Glycerin, 6.6% w/v | 936 |

EXAMPLE 2

In Vitro Imaging Studies

A Toshiba ultrasound machine (Sonolayer SSA270A) with a 5 MHz curved array transducer (Toshiba PVF575MT) was used together with a phantom to characterize the acoustical properties of the solutions. The phantom used is a rectangular block made out of tissue mimicking material through which a 3 centimeter diameter cylindrical well extends which represents a body cavity. A graphic representation of the images produced using the phantom is depicted in FIG. 1.

The ultrasound instrument was used in B-mode with a single electronic focus at 5.7 cm. The parameter settings used to obtain the data are listed in Table 2. Except for the power setting, which was maximized for these in vitro studies, the parameters listed are typical of those that would be used as initial settings for an abdominal scan in a clinical setting. The depth gain compensation (DGC) settings were determined in a set-up background check performed with water prior to each ultrasonic study by adjusting them up or down to obtain an equal backscattering signal intensity throughout an image sector slice of the phantom.

TABLE 2

| Toshiba Ultrasound Instrument Settings | |
|---|---|
| Parameter | Setting |
| Power | 16 |
| Depth | 12 cm |
| Frame Rate | 18 Hz |
| Transducer | C 5.00 |
| Persistence | 5 |
| Edge Enhancement | 0 |
| Post Process | 4 |
| Dynamic Range | 70 |
| Receive Gain | 88 |

All of the values reported below in Table 3 are average intensities extracted from histogram measurements obtained by utilizing the software (SSA-270A, version 7.01, measurement menu) provided with the Toshiba ultrasound instrument. The histogram measurement provides a plot of the number of pixels vs signal intensity for a region of interest (ROI) within the image sector chosen by the operator. From this histogram, the mean intensity and the standard deviation within the ROI are determined.

All of the samples listed in Table 1 were first degassed under vacuum and examined at room temperature for their backscattering signal strength and degree of attenuation. Degassed water was used as the reference sample, since it is known to show minimal attenuation and backscatter. A sample was gently poured into the phantom cavity (approximately 80 mL). Two to three minutes were allowed for the clearing of bubbles which may have been introduced while pouring. The transducer was placed on the front scanning window of the phantom block. The image observed with the transducer in this position was frozen onto the monitor. A histogram was then generated for three identically sized ROIs within the image sector. Values for the backscattering signal strength and attenuation are obtained from the mean intensity values produced with these histograms. An illustration of the image sector which shows the placement of the ROIs is provided in FIG. 1. ROI 1 depicts the phantom cavity which contains the test solution. ROI 2 depicts an area between the transducer and ROI 1. ROI 3 depicts an area further from the transducer than ROI 1.

To determine the backscatter factor, a measurement of signal intensity of the sample was obtained by selecting an ROI at the position which corresponds to the cavity, i.e., ROI 1. This value was interpreted as the strength of the sample's backscattering signal and is reported in Table 3 as the backscatter factor relative to the degassed water control (ROI $1_{sample}$ divided by ROI $1_{water}$). Attenuation factors expressed as a percentage were obtained by subtracting the mean intensity values of ROI 2 from that of ROI 3, and then dividing by ROI 2. Note that the intensity measurements in ROI 2 and 3 are a measure of the ultrasound beam before and after it interacts with the sample, respectively. A value of about +5% to about −25% indicates little or no attenuation.

TABLE 3

| Backscattering & Attenuation | | |
|---|---|---|
| Sample | Backscattering Intensity Factor | Attenuation Factor |
| Water | 1.00 | +3.0% |
| Polydextrose | .88 | +3.0% |
| Corn Syrup | .86 | +1.3% |
| Maltodextrin | .83 | −20.9% |
| Glycerin | .94 | +5.0% |

EXAMPLE 3

In Vivo Imaging Studies

In vivo properties of the solutions were determined in a subject who had fasted for 8–12 hours prior to ingesting 250 mL of each solution which had been degassed under vacuum prior to use. Ultrasound imaging was performed in the upright standing position throughout the procedure.

B-mode ultrasound imaging of the gastrointestinal tract and surrounding tissues and organs was done with a Toshiba 5 MHz curved array transducer (Toshiba PVF-575MT) coupled to a Toshiba Sonolayer Ultrasound instrument with SSA-270A version 7.01 software. Images were videotaped immediately prior to ingestion of the test solutions (time 0) and at five minute intervals thereafter. DGC settings were optimized to give a clear image of the gastrointestinal tract, in particular the stomach, and adjacent tissues/organs with depth settings of either 10 or 12 cm. From the videotaped images, estimates of the stomach size were obtained by capturing a longitudinal image of the organ and measuring the area within the stomach lining. The value determined for each time point was normalized by division by the time 0 value. These data are summarized in Table 4 and are depicted graphically in FIG. 2.

TABLE 4

Effect of Contrast Agents on Stomach Size

| TIME (MINUTES) | 0 | 5 | 10 | 15 | 20 |
|---|---|---|---|---|---|
| Water | 1.00 | 0.89 | 0.93 | 0.92 | nd |
| 50% (w/v) Maltodextrin | 1.00 | 1.89 | 1.75 | 1.69 | 1.73 |
| 25% (w/v) Polydextrose | 1.00 | 2.28 | 2.56 | 2.64 | 2.55 |

Figure 2:
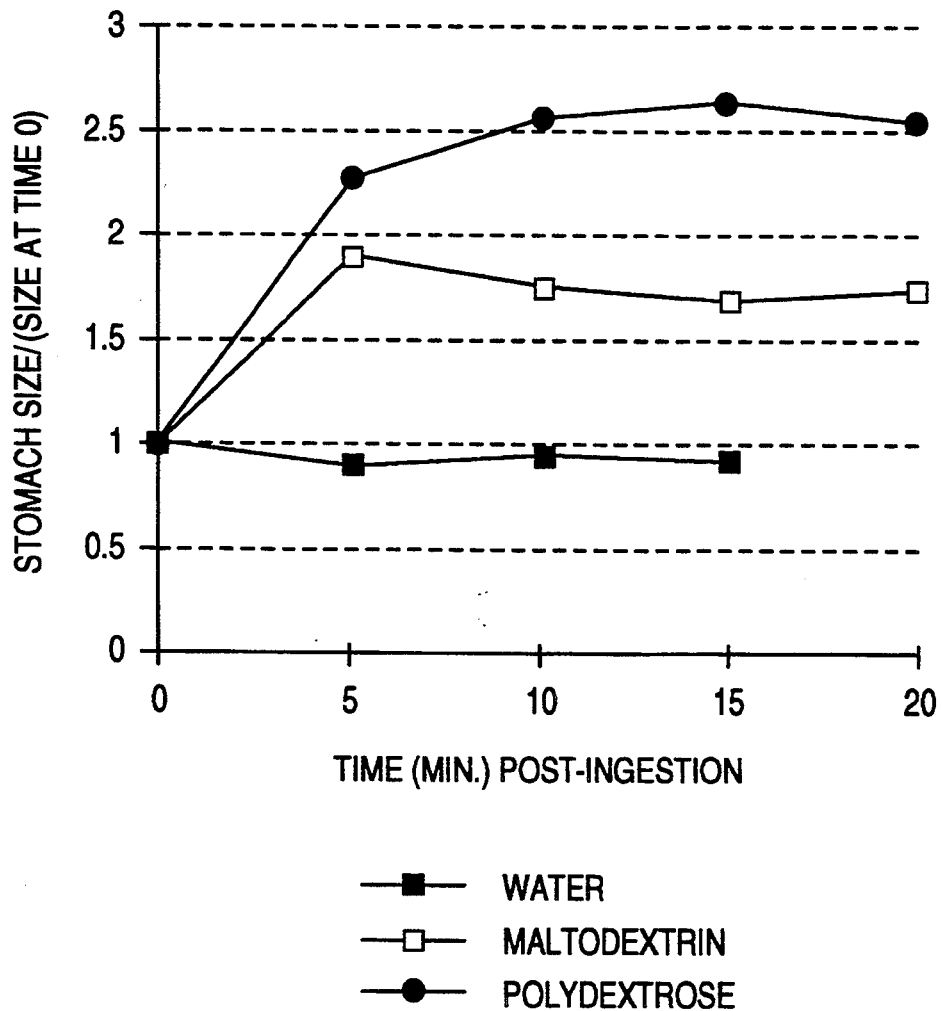

The data in Table 4 and FIG. 2 demonstrate that the maltodextrin and polydextrose solutions have gastric emptying times of greater than 20 minutes. With each of these solutions, an immediate apparent increase in stomach size was observed which was maintained for at least 20 minutes. In comparison, when the same volume of water was ingested, no increase in stomach dimensions was observed due to the fact that the water is rapidly clearing from the stomach.

Shortly after ingestion of either maltodextrin or polydextrose solutions, the stomach lumen became sonolucent and nonechogenic and thus appeared "black" in the ultrasonic image. The stomach wall was clearly demarcated from the stomach lumen and the individual layers of the stomach mucosa were easily differentiated. Gas and particulates present in the stomach before ingestion which previously caused attenuation and artifactual backscatter of the ultrasonic signal were completely displaced by the solution allowing complete sonographic visualization through the stomach to the upper abdominal organs. In particular, the pancreas which was not discernible in the absence of the solution became clearly visible. After thirty minutes or longer, the negative image effect caused by the presence of the solutions became visible in the small bowel allowing for visualization of the bowel wall.

We claim:

1. (Amended) A method of ultrasonic imaging of tissue defining the gastrointestinal tract and organs in the upper abdominal region comprising:

a) introducing a sufficient amount of a chemically defined essentially sonolucent and nonechogenic ultrasound contrast agent solution that is stable under gastric conditions and has a gastric emptying time of at least about twenty minutes into the stomach to substantially fill the stomach and remove gas by displacement, dispersion and absorption from the imaging field;

b) applying ultrasonic energy to the stomach and upper abdominal region while said solution is present in the gastrointestinal tract, said energy passing through the solution and being reflected by said tissue and said organs; and c) forming an image from the reflected energy.

2. The method of claim 1 wherein the gastric emptying time is about twenty minutes to two hours.

3. The method of claim 1 wherein the solution has an osmolality $\geq 300$ millimoles per kilogram.

4. The method of claim 1 wherein the solution is degassed prior to introduction.

5. The method of claim 1 wherein said solution contains a solute selected from the group consisting of polydextrose, maltodextrin, corn syrup, glycerin and mixtures thereof.

6. The method of claim 5 wherein the concentration of the solute is 10% to 50% weight per volume.

7. The method of claim 1 wherein said solution contains polydextrose.

8. The method of claim 1 wherein said solution contains maltodextrin.

9. The method of claim 1 wherein said solution contains corn syrup.

10. The method of claim 1 wherein said solution contains glycerin.

11. The method of claim 1 wherein said solution contains an acid selected from the group consisting of amino acids and fatty acids.

12. The method of claim 1 wherein said solution contains an amino acid.

13. The method of claim 1 wherein said solution contains a fatty acid.

14. The method of claim 1 wherein said solution contains a glyceride.

15. The method of claim 1 wherein said solution contains a monoglyceride.

16. The method of claim 1 wherein said solution contains a diglyceride.

17. The method of claim 1 wherein said solution contains a triglyceride.

18. The method of claim 1 wherein said solution contains L-tryptophan.

19. The method of claim 1 wherein said solution contains an agent that binds calcium ions at gastric pH.

* * * * *